United States Patent
Sargeant

(10) Patent No.: US 10,314,682 B2
(45) Date of Patent: Jun. 11, 2019

(54) SYSTEM AND METHOD HAVING AN ELECTROMAGNETIC MANIPULATOR WITH A UV TACKING MECHANISM

(71) Applicant: Covidien LP, Mansfield, MA (US)

(72) Inventor: Timothy Sargeant, Guilford, CT (US)

(73) Assignee: Covidien LP, Mansfield, MA (US)

( * ) Notice: Subject to any disclaimer, the term of this patent is extended or adjusted under 35 U.S.C. 154(b) by 385 days.

(21) Appl. No.: 14/248,767

(22) Filed: Apr. 9, 2014

(65) Prior Publication Data

US 2014/0309626 A1 Oct. 16, 2014

Related U.S. Application Data

(60) Provisional application No. 61/811,134, filed on Apr. 12, 2013.

(51) Int. Cl.
*A61F 2/00* (2006.01)
*A61B 17/00* (2006.01)
(Continued)

(52) U.S. Cl.
CPC .......... *A61F 2/0063* (2013.01); *A61B 17/068* (2013.01); *A61B 18/18* (2013.01);
(Continued)

(58) Field of Classification Search
CPC ........ A61B 2017/086; A61B 2017/005; A61B 17/00234; A61B 2018/1807;
(Continued)

(56) References Cited

U.S. PATENT DOCUMENTS

| 4,273,110 A | 6/1981 | Groux |
| 5,851,218 A | 12/1998 | Lev |

(Continued)

FOREIGN PATENT DOCUMENTS

| WO | WO 2005/074814 A2 | 8/2005 | |
| WO | WO 2009036094 A2 * | 3/2009 | ........... A61F 2/0063 |

OTHER PUBLICATIONS

Extended European Search Report for EP 12 16 3852 dated Aug. 13, 2012.
(Continued)

*Primary Examiner* — Lynsey C Eiseman
*Assistant Examiner* — Amanda L Steinberg

(57) ABSTRACT

A surgical instrument is provided including a handle portion and a body portion extending distally from the handle portion and defining a longitudinal axis. The surgical instrument also includes an end effector assembly disposed at a distal end of the body portion, the end effector assembly including an electromagnetic manipulator in cooperation with an ultraviolet (UV) light source for performing tacking of an implant. In an alternative embodiment, the end effector assembly includes an electromagnetic manipulator in cooperation with at least one tack for performing tacking of an implant. The implant may be a mesh having a ferromagnetic coating activated by the electromagnetic manipulator. The tissue may have a UV coating activated by UV light applied by the UV light source.

3 Claims, 6 Drawing Sheets

(51) Int. Cl.
   *A61B 18/18* (2006.01)
   *A61B 17/064* (2006.01)
   *A61B 17/068* (2006.01)

(52) U.S. Cl.
   CPC ............... *A61B 2017/005* (2013.01); *A61B 2017/00876* (2013.01); *A61B 2017/0647* (2013.01); *A61B 2018/1807* (2013.01); *A61F 2002/0072* (2013.01)

(58) Field of Classification Search
   CPC .... A61B 2018/1861; A61B 2017/0648; A61B 2017/0876; A61B 2017/0647; A61B 17/085; A61F 2002/0072
   See application file for complete search history.

(56) References Cited

U.S. PATENT DOCUMENTS

| | | | |
|---|---|---|---|
| 5,928,261 A | 7/1999 | Ruiz | |
| 5,972,007 A * | 10/1999 | Sheffield | A61F 2/0063 606/151 |
| 6,110,188 A * | 8/2000 | Narciso, Jr. | A61B 17/11 606/153 |
| 6,709,128 B2 | 3/2004 | Gordon et al. | |
| 6,719,765 B2 * | 4/2004 | Bonutti | A61B 17/04 606/144 |
| 6,981,867 B2 | 1/2006 | Cao | |
| 7,182,597 B2 | 2/2007 | Gill et al. | |
| 7,273,369 B2 | 9/2007 | Rosenbiood et al. | |
| 7,332,689 B2 | 2/2008 | Mertens et al. | |
| 7,427,262 B2 | 9/2008 | Bonningue et al. | |
| 7,677,888 B1 | 3/2010 | Halm | |
| 7,753,936 B2 | 7/2010 | Voegele et al. | |
| 8,113,830 B2 | 2/2012 | Gill et al. | |
| 2003/0105474 A1 | 6/2003 | Bonutti | |
| 2006/0085005 A1 | 4/2006 | Kenealy, III et al. | |
| 2006/0212113 A1 | 9/2006 | Shaolian et al. | |
| 2006/0286137 A1 | 12/2006 | Sandhu et al. | |
| 2007/0039286 A1 * | 2/2007 | DeMasi, Sr. | B25C 11/00 52/750 |
| 2007/0088193 A1 | 4/2007 | Omori et al. | |
| 2007/0239154 A1 | 10/2007 | Shaolian | |
| 2008/0039854 A1 | 2/2008 | Rabiner | |
| 2008/0306333 A1 | 12/2008 | Chin | |
| 2008/0319259 A1 | 12/2008 | Goto | |
| 2009/0248060 A1 * | 10/2009 | Schneider | A61F 2/013 606/200 |
| 2010/0012703 A1 | 1/2010 | Calabrese et al. | |
| 2010/0063500 A1 | 3/2010 | Muszala | |
| 2010/0114126 A1 * | 5/2010 | Neff | A61B 17/52 606/151 |
| 2010/0286691 A1 * | 11/2010 | Kerr | A61B 18/1206 606/51 |
| 2011/0174313 A1 * | 7/2011 | von Pechmann | A61B 17/00234 128/834 |
| 2011/0293687 A1 * | 12/2011 | Bennett | A61K 9/06 424/423 |
| 2012/0179214 A1 * | 7/2012 | Geist | A61B 17/7002 606/86 A |
| 2012/0271290 A1 | 10/2012 | Sargeant | |

OTHER PUBLICATIONS

European Search Report for 14164481.5 date of completion is Oct. 21, 2014 (4 pages).
Partial European Search Report dated Jul. 2, 2014 for EP 14 16 4481.
European Office Action and Summary for EP 14 164 481.5 dated Nov. 16, 2015.
European Office Action for EP 14 164 481.5 dated Jun. 20, 2016.
Chinese Office Action dated Mar. 31, 2017 in corresponding Chinese Patent Application No. 201410148867.1 together with English translation, 19 pages.
Chinese Office Action dated Sep. 11, 2017 issued in corresponding Chinese Application No. 2014101488671.
Australian Examination Report issued in Australian Application No. 2014202039 dated Jan. 17, 2018.

* cited by examiner

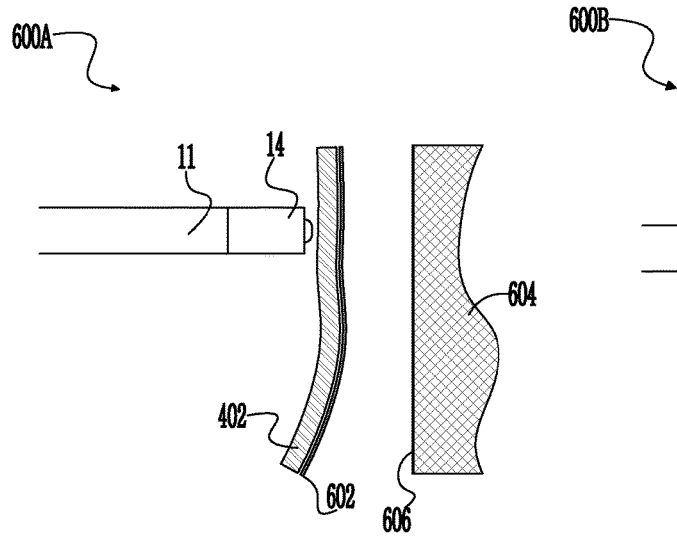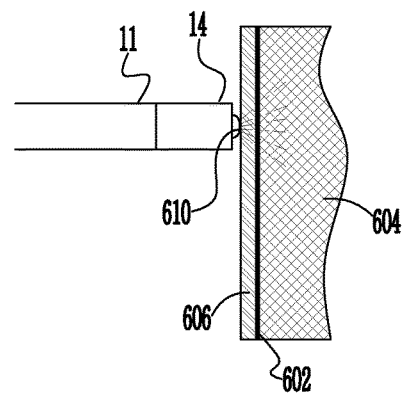
FIG. 6A  FIG. 6B
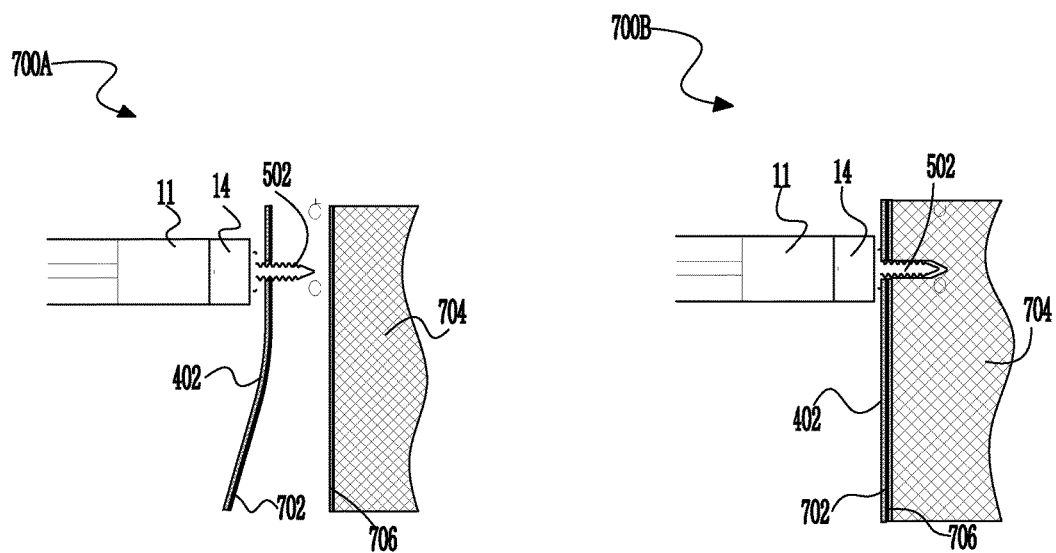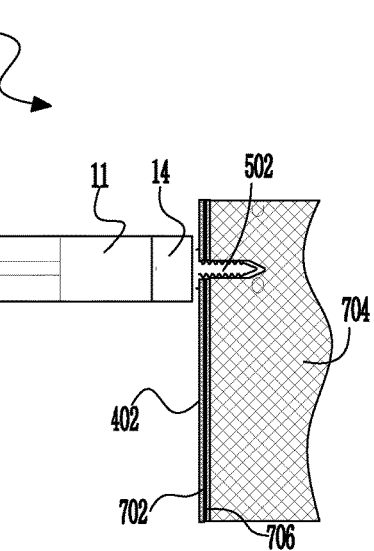
FIG. 7A  FIG. 7B

SYSTEM AND METHOD HAVING AN ELECTROMAGNETIC MANIPULATOR WITH A UV TACKING MECHANISM

CROSS-REFERENCE TO RELATED APPLICATIONS

This application claims priority to, and the benefit of, U.S. Provisional Patent Application Ser. No. 61/811,134, filed Apr. 12, 2013, the entire contents of which is incorporated by reference herein.

BACKGROUND

Technical Field

The present disclosure relates to endoscopic surgical instruments. More particularly, the present disclosure relates to a system and method for ultraviolet (UV) tacking an implant via an endoscopic surgical instrument having a UV light source mechanism and an electromagnetic manipulator distally disposed thereon.

Background of Related Art

Surgical instruments which include a tool assembly mounted on a distal end of a body portion of the surgical instrument for articulation are well known. Typically, such surgical instruments include articulation control mechanisms, which allow an operator to remotely articulate the tool assembly in relation to the body portion of a surgical instrument to allow the operator to more easily access, operate on, and/or manipulate tissue.

Such articulating tool assemblies have become desirable, especially in the endoscopic surgical procedures. In an endoscopic surgical procedure, the distal end of a surgical instrument is inserted through small incisions in the body to access a surgical site. Typically, an appropriately sized cannula, e.g., 5 mm, 10 mm, etc., is inserted through the body incision to provide a guide channel for accessing the surgical site. Because it is desirable to provide small body incisions, i.e., less scarring, reduced trauma to the patient, faster healing time, the tolerances between the surgical instrument and the inner diameter of the cannula are small.

Conventional articulating tool tips have limited functionality mainly due to mechanical design limitations of actuating mechanisms. Thus, it is desirable to provide an articulating surgical instrument, which includes an articulation mechanism that would provide a wider range of functions for the articulation tip.

SUMMARY

Accordingly, an improved surgical instrument is provided. The surgical instrument includes a handle portion and a body portion extending distally from the handle portion and defining a longitudinal axis. The surgical instrument also includes an end effector assembly disposed at a distal end of the body portion, the end effector assembly including an electromagnetic manipulator in cooperation with an ultraviolet (UV) light source for performing tacking of an implant.

In another exemplary embodiment, the implant is a mesh and the mesh includes material with ferromagnetic properties.

In another exemplary embodiment, the implant is a mesh having a ferromagnetic coating. The ferromagnetic coating is responsive to electromagnetism emitted from the electromagnetic manipulator.

In another exemplary embodiment, when the mesh is positioned in proximity to the electromagnetic manipulator to be placed at a surgical site, the mesh is exposed to the UV light emitted from the UV light source such that the tacking of the mesh to the surgical site is performed.

In another exemplary embodiment, at least one sensor is adapted to continuously or intermittently monitor UV light emission from the UV light source.

In yet another exemplary embodiment, a trigger mechanism is positioned on the handle portion for selectively activating the UV light source and the electromagnetic manipulator.

Moreover, the implant has a positive charge coating with methacrylate, whereas tissue of a surgical site has a negative charge coating with methacrylate for attracting the implant.

Additionally, another improved surgical instrument is provided. The surgical instrument includes a handle portion and a body portion extending distally from the handle portion and defining a longitudinal axis. The surgical instrument also includes an end effector assembly disposed at a distal end of the body portion, the end effector assembly including an electromagnetic manipulator in cooperation with at least one tack for performing tacking of an implant.

Moreover, a tip of the at least one tack includes an electromagnet incorporated therein. The implant is a mesh having a ferromagnetic coating. The ferromagnetic coating is attracted by the electromagnetic manipulator in an energized/activated state.

In another exemplary embodiment, when the mesh is positioned in proximity to the electromagnetic manipulator to be placed at a surgical site, the mesh is exposed to electromagnetism emitted from the electromagnetic manipulator such that the mesh may be repositioned in the surgical site.

In yet another exemplary embodiment, a method of UV tacking a mesh at a surgical site is provided. The method includes the steps of applying energy to a handle portion of a surgical instrument having a body portion extending distally therefrom, introducing an end effector assembly at a distal end of the body portion, incorporating a UV light source and an electromagnetic manipulator at the end effector assembly, selectively applying electromagnetism via the electromagnetic manipulator to the mesh, selectively applying a UV light emitted from the UV light source to the mesh and tacking the mesh to the surgical site. The mesh includes a ferromagnetic coating that is responsive to exposure to the electromagnetism emitted from the electromagnetic manipulator.

In yet another exemplary embodiment a method of tacking a mesh at a surgical site is provided. The method includes the steps of applying energy to a handle portion of a surgical instrument having a body portion extending distally therefrom, introducing an end effector assembly at a distal end of the body portion, incorporating at least one tack and an electromagnetic manipulator at the end effector assembly, selectively applying electromagnetism via the electromagnetic manipulator to the mesh, selectively applying the at least one tack to the mesh and tacking the mesh to the surgical site. The mesh includes a ferromagnetic coating that is responsive to exposure to the electromagnetism emitted from the electromagnetic manipulator.

BRIEF DESCRIPTION OF THE DRAWINGS

The accompanying drawings, which are incorporated in and constitute a part of this specification, illustrate embodiments of the disclosure and, together with a general description of the disclosure given above, and the detailed description of the embodiment(s) given below, serve to explain the principles of the disclosure, wherein:

FIG. 6A is a perspective view of a portion of the surgical instrument of FIG. 1 electromagnetically grasping the mesh and applying a UV light thereafter to the tissue, the mesh having a positive charge coating and the tissue having a negative charge coating, in accordance with the present disclosure;

FIG. 6B is a side view of FIG. 6A illustrating the positive charged mesh placed on negative charged tissue of the surgical site, in accordance with the present disclosure;

FIG. 7A is a perspective view of a portion of the surgical instrument of FIG. 1 electromagnetically grasping the mesh and applying a tack thereafter, the mesh having a positive charge coating and the tissue having a negative charge coating, in accordance with the present disclosure; and FIG. 7B is a side view of FIG. 7A illustrating the positive charged mesh placed on negative charged tissue of the surgical site including a tack, in accordance with the present disclosure.

DETAILED DESCRIPTION

Figure 1:
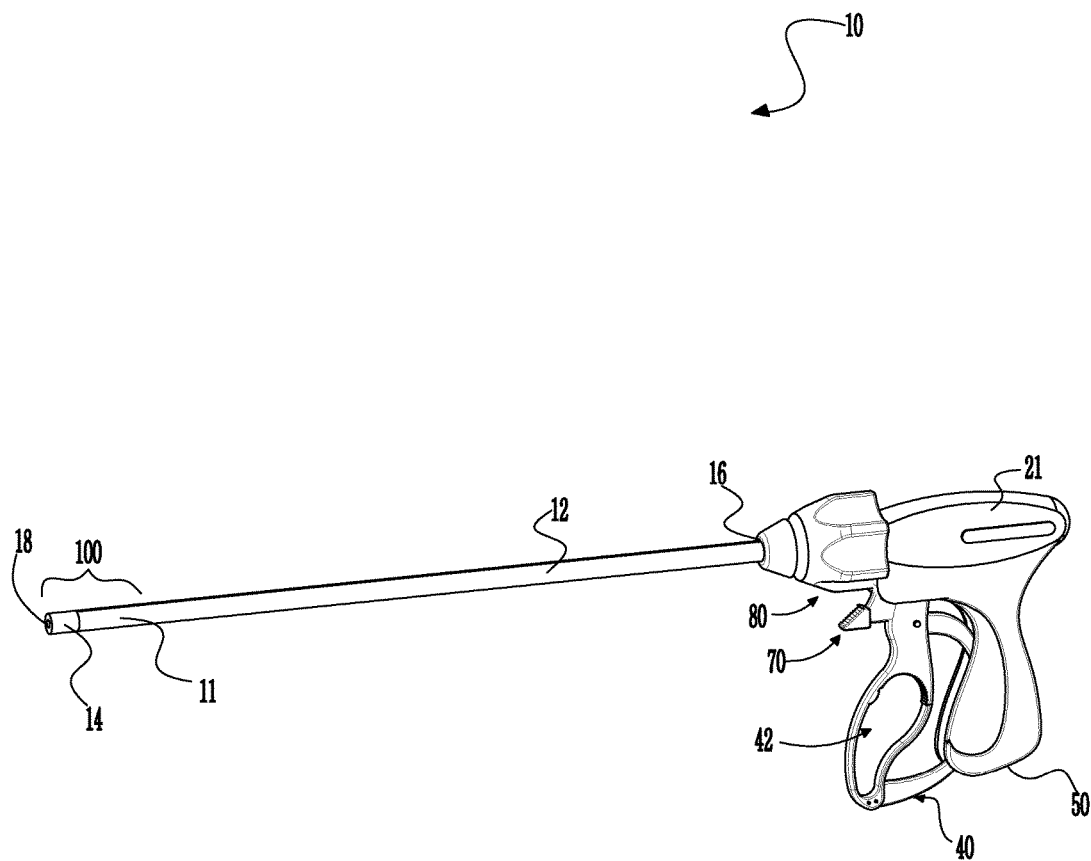
FIG. 1 is a perspective view of a surgical instrument having an electromagnetic manipulator and a UV light source, in accordance with the present disclosure.

Embodiments of the presently disclosed apparatus will now be described in detail with reference to the drawings, in which like reference numerals designate identical or corresponding elements in each of the several views. As used herein, the term "distal" refers to that portion of the tool, or component thereof which is further from the user while the term "proximal" refers to that portion of the tool or component thereof which is closer to the user.

Referring to FIG. 1, a surgical system for use in a surgical procedure, e.g., a minimally invasive procedure is illustrated.

FIG. 1 shows a surgical instrument 10 according to the present disclosure. More particularly, surgical instrument 10 generally includes a housing 21, a handle assembly 40, a rotating assembly 80, and a trigger assembly 70, which mutually cooperate with the end effector assembly 100.

The surgical instrument 10 also includes a shaft 12, which has a distal end 11 that mechanically engages the end effector assembly 100 and a proximal end 16 that mechanically engages the housing 21 proximate the rotating assembly 80. Handle assembly 40 includes a fixed handle 50 and a movable handle 42. Handle 42 moves relative to the fixed handle 50 to actuate the end effector assembly 100.

The end effector assembly 100 further includes an electromagnetic manipulator 14 and an ultraviolet (UV) light source 18 (or UV light mechanism). The surgical instrument 10 also includes the trigger 70, which may be configured to selectively activate the electromagnetic manipulator 14 and the UV light source 18 disposed at the distal end 11 of the effector assembly 100. The electromagnetic manipulator 14 may operate in cooperation with the UV light source 18 for performing tacking of an implant or mesh (see FIGS. 3A and 3B). In particular, the electromagnetic manipulator 14 has an energized or activated state and a de-energized or de-activated state. In the activated state, the electromagnetic manipulator 14 is a source of electromagnetism that attracts ferromagnetic materials. In the de-activated state, the electromagnetic manipulator 14 does not attract ferromagnetic materials. The power source for the UV light source 18 and the electromagnetic manipulator 14 may be self-contained within the handle 42.

Energy is transmitted to the implant or mesh (see FIGS. 4A-7B) from one or more energy transmission devices such as a laser or lasers. In at least one embodiment, the laser is a UV laser, however in some alternative embodiments the laser may be an IR laser, diode laser, $CO_2$, visible light, or any other form of laser device or combinations thereof. One skilled in the art may contemplate using a plurality of different forms of energy in order to tack the implant or mesh to the incision of the surgical site. For example, one skilled in the art may use thermal energy, microwave energy, chemical energy, and/or ultrasonic energy or a combination thereof.

Referring back to FIG. 1, the surgical instrument 10 also includes the rotating assembly 80 mechanically associated with the shaft 12 and the drive assembly (not shown). Movement of the rotating assembly 80 imparts similar rotational movement to the shaft 12 which, in turn, rotates the end effector assembly 100.

It is envisioned that the surgical instrument 10 may be designed such that it is fully or partially disposable depending upon a particular purpose or to achieve a particular result. For example, end effector assembly 100 may be selectively and releasably engageable with the distal end 11 of the shaft 12 and/or the proximal end 16 of the shaft 12 may be selectively and releasably engageable with the housing 21 and handle assembly 40. In either of these two instances, the surgical instrument 10 may be either partially disposable or reposable, such as where a new or different end effector assembly 100 or end effector assembly 100 and shaft 12 are used to selectively replace the old end effector assembly 100 as needed.

Figure 2:
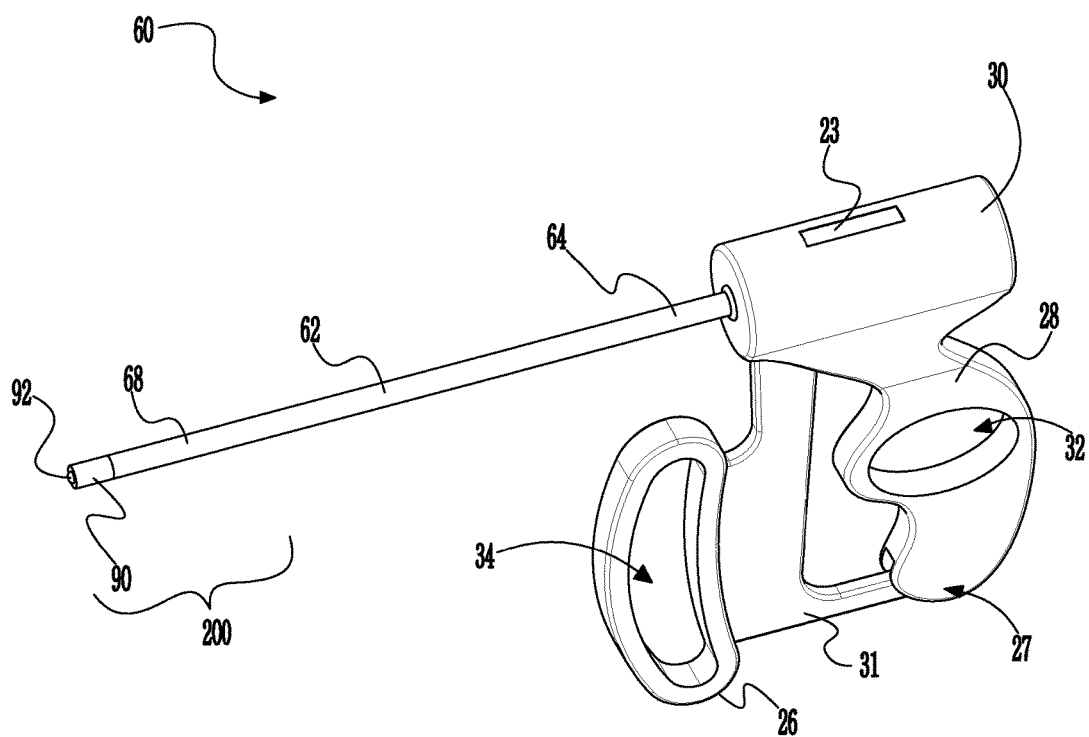
FIG. 2 is a perspective view of another surgical instrument having an electromagnetic manipulator and a UV light source, in accordance with the present disclosure.

Referring to FIG. 2, a perspective view of another surgical instrument 60 having an electromagnetic manipulator 90 and UV light source 92, in accordance with the present disclosure is presented. Electromagnetic manipulator 90 functions substantially similar to electromagnetic manipulator 14 as described above.

An endoscopic instrument according to this embodiment of the present disclosure is designated generally as reference numeral 60. Endoscopic instrument 60 includes an elongated shaft 62 having a proximal end 64 that mechanically couples to a housing in the form of a handle assembly 30, and a distal end 68 that is configured to receive and mechanically couple to a detachable end effector assembly 200 that includes an electromagnetic manipulator 90 and a UV light source 92.

Shaft 62 is a generally tubular hollow structure defining an axial passageway therethrough. Shaft 62 supports an end effector assembly 200 at a distal end thereof such that end effector assembly 200 may be properly engaged thereto and detachable therefrom. In this instance, shaft 62, or a portion thereof, may have one or more portions that are capable of articulating and/or pivoting.

Handle assembly 30 mechanically engages proximal end 68 of shaft 62 and includes a movable handle 26 for activating the electromagnetic manipulator 90 and a UV light source 92. Movable handle 26 includes an aperture 34 configured for receiving one or more of an operator's fingers. Movable handle 26 is selectively movable from a first position relative to a fixed handle 28 to a second position in closer proximity to the fixed handle 28 to activate the electromagnetic manipulator 90 and a UV light source 92.

The internal mechanically cooperating components associated with the movable handle 26 to activate the electromagnetic manipulator 90 and a UV light source 92 is commonly known and may include any number of gears, links, springs, and/or rods such that endoscopic device 60 may function as intended. In embodiments, attached to movable handle 26 is a guide 31. Guide 31 serves to maintain movable handle 26 in alignment with fixed handle 28. To this end, fixed handle includes a channel 27 that extends proximally for receiving guide 31 of movable handle 26. It is contemplated that additional mechanisms, such as, for example, hydraulic, semi-hydraulic and/or gearing systems may be employed to control and/or limit the movement of handle 26 relative handle 28.

Fixed handle 28 includes an aperture 32 configured for receiving one or more of an operator's fingers (e.g., a thumb). Fixed handle 28 provides a gripping surface for an operator's hand such that an operator may effectively manipulate the endoscopic apparatus 60 internal or external a patient. While the drawings depict movable handle 26 and fixed handle 28 having apertures 34, 32, respectively, it is within the purview of the present disclosure that one or both of the handles 26, 28 may have solid configurations.

A release mechanism in the form of a button 23 is in mechanical and/or electrical communication with handle assembly 30 for selectively causing end effector assembly 200 to detach from the distal end 68 of shaft 62 when button 23 is actuated (e.g., via pressing, pushing, sliding, or any other suitable actuating motions). The internal mechanically cooperating component(s) associated with each of the release mechanism 23 and/or shaft 62 to detach the end effector assembly 200 from the distal end 68 of shaft 62 is commonly known and may include any number of gears, links, drive rods, springs, and so forth such that endoscopic apparatus 60 may function as intended. Button 23 may include any number of grooves, ribs, protrusions and the like configured to facilitate actuation thereof.

The end effector assembly 200 further includes an electromagnetic manipulator 90 and an ultraviolet (UV) light source 92. The surgical instrument 60 also includes the guide 31, which selectively activates the electromagnetic manipulator 90 and the UV light source 92 disposed at the distal end 11 of the end effector assembly 200. The electromagnetic manipulator 90 may operate in cooperation with the UV light source 92 for performing tacking of an implant or mesh (see FIGS. 3A and 3B).

Energy is transmitted to the implant or mesh (see FIGS. 4A-7B) from one or more energy transmission devices such as a laser or lasers. In at least one embodiment, the laser is a UV laser, however in some alternative embodiments the laser may be an IR laser, diode laser, $CO_2$, visible light, or any other form of laser device or combinations thereof. One skilled in the art may contemplate using a plurality of different forms of energy in order to tack the implant or mesh to the incision of the surgical site. For example, one skilled in the art may use thermal energy, microwave energy, chemical energy, and/or ultrasonic energy or a combination thereof.

Figure 3A:
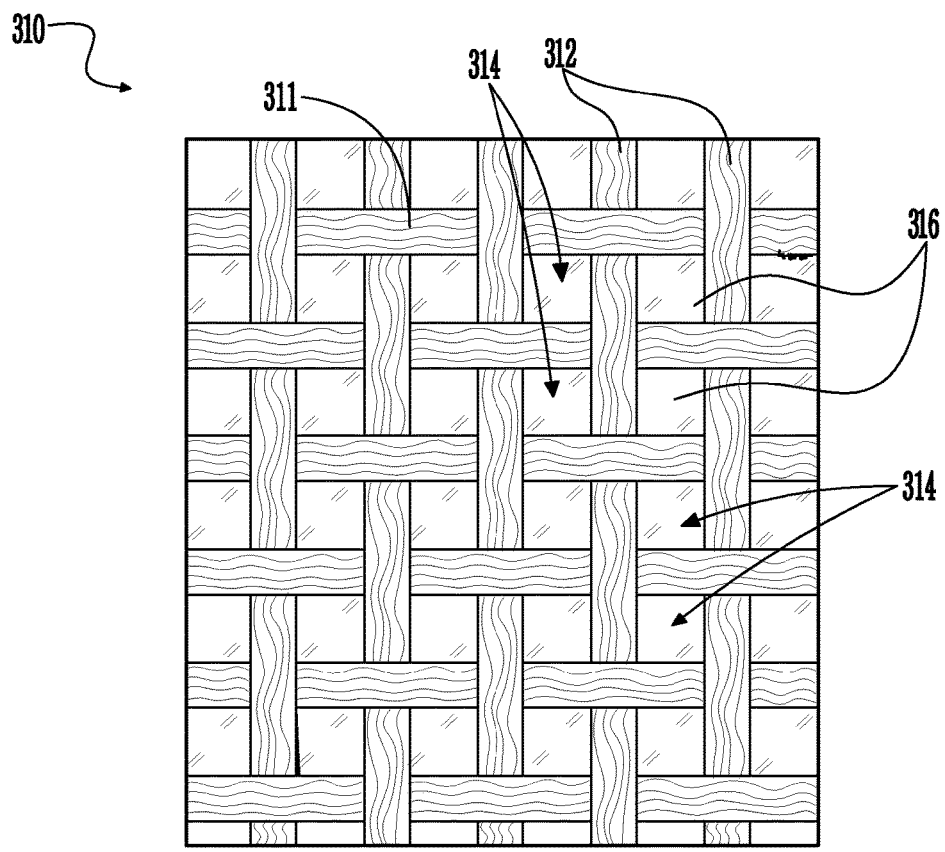
FIG. 3A is a perspective view of the mesh, in accordance with the present disclosure.
Figure 3B:
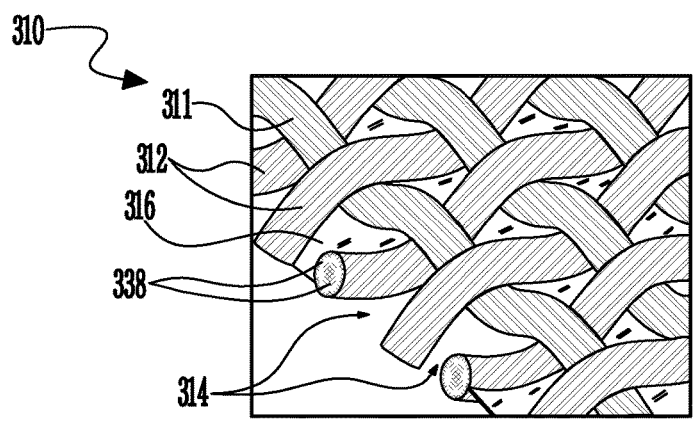
FIG. 3B is a perspective cross-sectional view of the mesh of FIG. 3A, in accordance with the present disclosure.

Referring to FIG. 3A, a perspective view of the mesh 300, in accordance with the present disclosure is presented, whereas referring to FIG. 3B a perspective cross-sectional view of the mesh 300 of FIG. 3A, in accordance with the present disclosure is presented.

The surgical mesh 300 (or implant) is suitable for surgical repair of hernias and other surgical procedures requiring reinforcement or repair of soft tissue, such as muscle or wall tissue defects, pelvic organ prolapse, and urinary incontinence, for example. The mesh 300 of the present disclosure may be in the form of sheets, patches, slings, suspenders, and other implants and composite materials such as pledgets, buttresses, wound dressings, drug delivery devices, and the like. The present surgical mesh 300 may be implanted using open surgery or by a laparoscopic procedure.

The surgical mesh 300 may be fabricated from monofilament and/or multifilament yarns 312, which may be made of any suitable biocompatible material. Suitable materials from which the mesh 300 may be made should have the following characteristics: sufficient tensile strength to support tissue; sufficiently inert to avoid foreign body reactions when retained in the body for long periods of time; easily sterilized to prevent the introduction of infection when the mesh 300 is implanted in the body; and sufficiently strong to avoid tearing of portions thereof.

Referring now to FIGS. 3A and 3B, the mesh 300 is illustrated including a porous mesh substrate 311. The substrate 311 may be formed from fibers, filaments, threads or yarns 312 defining a plurality of pores 314 therebetween. The yarns 312 of the substrate 311 may be made up of multiple filaments 338 (see FIG. 3B). The pores 314 may include one or more intra-pore films 316. The intra-pore films 316 of the present disclosure are non-contiguous with respect to one another, with each intra-pore film 316 being located in a single pore 314 of the porous substrate 311. In embodiments, multiple intra-pore films 316 may also be formed within each of the pores 314 of the substrate 311. The term "non-contiguous" as used herein, is used to denote one or more films 316 that are wholly contained within a corresponding pore 314 and are not in physical contact with another intra-pore film 316 of any other pore 314, as compared to a conventional film-coated porous substrate in which the film stretches across multiple pores. The intra-pore films 316 are solely contained within the pores of the substrate. The intra-pore film does not span across the yarns 312 of the substrate. The intra-pore films 316 are non-contiguous and are not bridged together by applying a film over the entire substrate, but rather, the intra-pore films 316 are created at discrete locations, within the individual pores.

The intra-pore films 316 may be formed at any plane within the pores 314 relative to the plane of the substrate 311 such that the intra-pore film 316 does not contact any adjacent intra-pore film 316. In embodiments, the intra-pore film 316 may be textured, smooth and/or porous.

In one embodiment, the yarns 312 may be made up of electromagnetic filaments in order to interact with the electromagnetic manipulator 14, 90. In other words, the mesh 300 includes magnetic properties in order to be grasped and/or manipulated by the electromagnetic manipulator 14, 90 of FIGS. 1 and 2.

As illustrated in FIG. 3A, not every pore 314 includes an intra-pore film. In certain embodiments, the pores including intra-pore films may be from about 10% to about 95% of the pores. In further embodiments, about 15% to about 90% of the pores of the substrate 311 include at least one intra-pore film. In other embodiments, from about 25% to about 75% of the pores of the substrate 311 include at least one intra-pore film. In other embodiments, all of the pores of the substrate 311 may include an intra-pore film.

The substrate 311 may include at least a center and a periphery. In embodiments where less than 100% of the pores of the substrate 311 include intra-pore films, the location of the intra-pore films may be random or patterned. For example, the pores of the substrate 311 that include the intra-pore films may be solely disposed in the center of the substrate 311 or the pores that include the intra-pore films may be solely disposed on the periphery of the substrate 311. In embodiments, the location of intra-pore films may be varied (e.g., random, patterned, etc.) depending upon the intended use of the substrate 311. The intra-pore films may form a discontinuous layer covering intermittent portions of the surface of the substrate 311. In one example, the intra-pore films may form a discontinuous layer on the surface of the substrate 311, wherein the porosity of the substrate 311 is maintained by the discontinuous layer of the intra-pore films.

Each intra-pore film 316 of a substrate 311 may be made from the same materials or different materials. In particular, one or more of the intra-pore films 316 may be formed from one material, while one or more different intra-pore films 316 may be formed from another material. The intra-pore film 316 may be permanent (e.g., non-bioabsorbable), biodegradable, or may be formed from any suitable combination of natural, synthetic, biodegradable and non-biodegradable materials. In the present application, the terms "biodegradable," "bioresorbable," and "bioabsorbable" are used interchangeably and are intended to mean the characteristic according to which an implant and/or a material is resorbed by biological tissues and the surrounding fluids, and disappears in vivo after a given period of time. The time period may vary, from about one minute to about several months or more, depending on the chemical nature of the implant and/or of the material utilized to form the implant.

In alternate embodiments, the substrate 311 may include intra-pore films that have a varying degradation rates, such that some of the intra-pore films degrade at a rate different from that of other intra-pore films. The type of material used to form the film, concentration of the material, and structure of the film, are some factors which may affect the degradation time of the film.

In some embodiments, the yarns 312 include at least two filaments which may be arranged to create openings therebetween, the yarns 312 also being arranged relative to each other to form openings in the mesh 300. Alternatively, the mesh 300 may be formed from a continuous yarn 312 that is arranged in loops that give rise to the openings in the mesh 300. The use of a mesh 300 having yarns 312 spaced apart in accordance with the present disclosure has the advantage of reducing the foreign body mass that is implanted in the body, while maintaining sufficient tensile strength to securely support the defect and tissue being repaired by the mesh 300. Moreover, the openings of the mesh 300 of the present disclosure may be sized to permit fibroblast throughgrowth and ordered collagen laydown, resulting in integration of the mesh 300 into the body. Thus, the spacing between the yarns 312 may vary depending on the surgical application and desired implant characteristics as envisioned by those skilled in the art.

All the above alternate embodiments of the mesh 300 may include one or more yarns 312 and/or pores 314 having magnetic properties embedded thereon and/or made up of electromagnetic filaments for responding to any type of electromagnetic manipulator 14, 90 of any type of surgical instrument/system 10, 60. Therefore, the mesh 300 may be any type of biodegradable polymeric coating having magnetic properties for interacting with electromagnetic manipulators 14, 90.

Figure 4A:
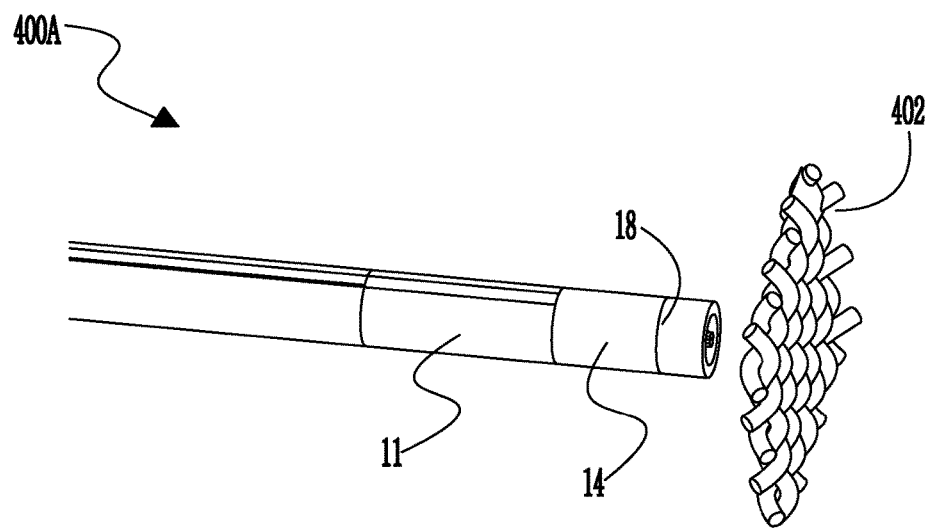
FIG. 4A is a perspective view of a portion of the surgical instrument of FIG. 1 electromagnetically grasping the mesh, in accordance with the present disclosure.
Figure 4B:
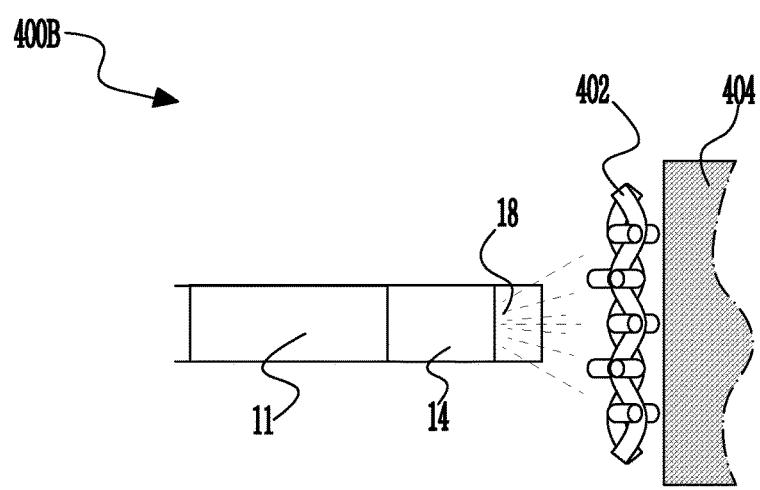
FIG. 4B is a side view of FIG. 4A illustrating the mesh placed on tissue of a surgical site and applying a UV light thereafter to the tissue, in accordance with the present disclosure.

Referring to FIG. 4A, a perspective view 400A of the surgical instrument 10 of FIG. 1 electromagnetically grasping the mesh 402 and applying a UV light thereafter to the tissue 404 is presented, whereas referring to FIG. 4B, a side view 400B of FIG. 4A illustrating the mesh 402 placed on tissue 404 of a surgical site is presented.

FIG. 4A depicts the distal end 11 of the surgical instrument 10 of FIG. 1 approaching the mesh 402. The distal end 11 of the surgical instrument 10 includes the electromagnetic manipulator 14 and a UV light source 18. The mesh 402 has magnetic properties. Energizing the electromagnetic manipulator 14 creates a magnetic field that attracts the mesh 402 due to the magnetic properties of the mesh 402. Activating the UV light source 18 produces UV light that cures the UV coating of the tissue to the mesh 402, such that the mesh 402 is attached to the tissue 404. Thus, the manipulator 14 is used for moving/placing/positioning the mesh 402, whereas the UV light source 18 is used for applying the UV light through the mesh 402 to cure the UV coating of the tissue 404 such that mesh 402 adheres to the tissue 404.

FIG. 4B depicts the mesh 402 placed on tissue 404. The surgeon manipulates the electromagnetic manipulator 14 in order to achieve proper placement of the mesh 402 on the tissue 404. The mesh 402 is placed on portions of tissue 404 that have a UV coating applied thereto. The types of coatings are described below. Once proper placement has been achieved, the surgeon may manipulate the trigger 70 to activate the UV light source 18. The activation of the UV light source 18 enables the UV light to be emitted from the distal end 11 to interact with the UV properties of the tissue 404. As such, the mesh 402 may be tacked to the tissue 404 via the UV light interacting with the UV coating of the tissue 404. Therefore, as stated above, the magnetic properties of the mesh 402 interact with the electromagnetic manipulator 14 such that the mesh 402 may be manipulated for grasping/positioning/placing the mesh 402 at the surgical site, and the UV properties of the UV coating of the tissue 404 are responsive to the UV light source for securely UV tacking the mesh 402 on the tissue 404 (or curing the UV coating of tissue 404 to the mesh 402).

Moreover, the mesh 402 has a ferromagnetic coating. The ferromagnetic coating responds to the electromagnetic manipulator 14 when the electromagnetic manipulator 14 is in the energized state. Further, the trigger mechanism 70 positioned on the handle assembly 30 is used for selectively activating the UV light source 18 and the electromagnetic manipulator 14.

Figure 5A:
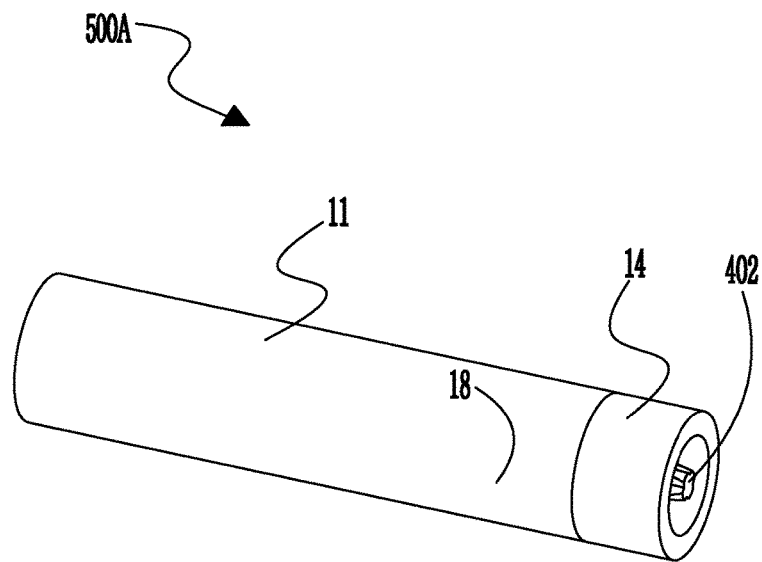
FIG. 5A is a perspective view of a portion of the surgical instrument of FIG. 1 electromagnetically grasping the mesh for placement adjacent to the tissue and applying a tack thereafter, in accordance with the present disclosure.
Figure 5B:
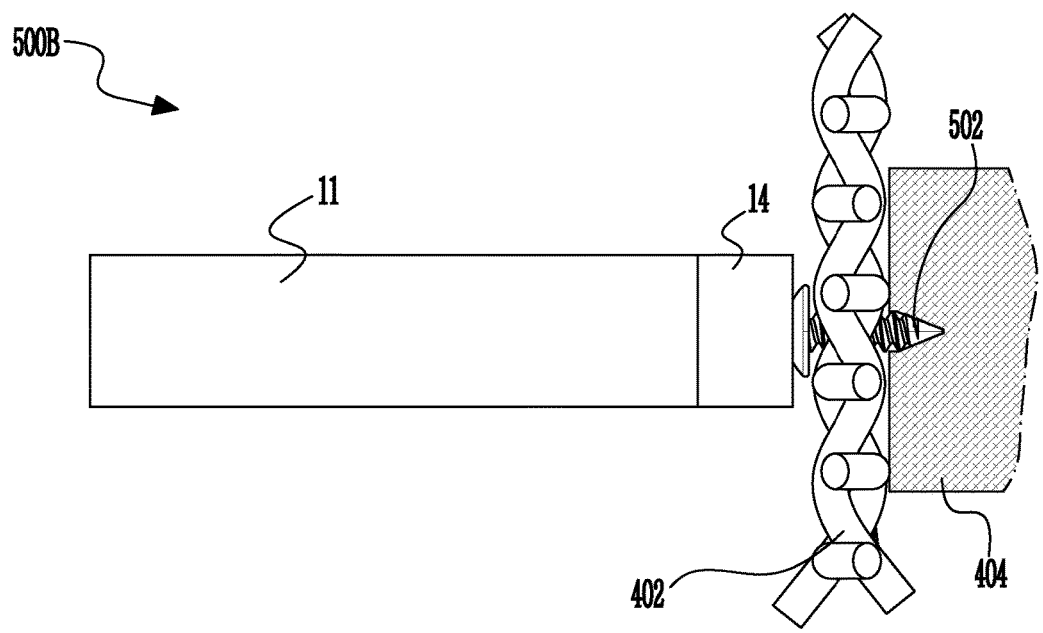
FIG. 5B is a side view of FIG. 5A illustrating the mesh and tack placed on tissue of the surgical site, in accordance with the present disclosure.

Referring to FIG. 5A, a perspective view 500A of the surgical instrument 10 of FIG. 1 electromagnetically grasping the mesh 402, placing the mesh 402 at the surgical site, and applying a tack 502 thereafter is presented, whereas referring to FIG. 5B, a side view 500B of FIG. 5A illustrating the mesh 402 and tack 502 placed on tissue 404 of the surgical site is presented.

FIG. 5A depicts the distal end 11 of the surgical instrument 10 of FIG. 1 approaching the mesh 402. The distal end 11 of the surgical instrument 10 includes the electromagnetic manipulator 14 having the tack 502 (instead of a UV light source as in FIG. 4A). The mesh 402 has magnetic properties.

FIG. 5B depicts the mesh 402 placed on tissue 404. The surgeon manipulates the electromagnetic manipulator 14 in order to achieve proper placement of the mesh 402 on the tissue 404. Once proper placement has been achieved, the surgeon may manipulate the trigger 70 to activate the electromagnetic manipulator 14. The tack 502 may include a ferromagnetic material, as described below. The activation of the electromagnetic manipulator 14 emits an electromagnetic field that interacts with the ferromagnetic material in the tack 502. When the electromagnetic manipulator 14 produces an electromagnetic field that has a polarity opposite that of the ferromagnetic material of the tack 502, the tack 502 is ejected from the distal end 11 of the surgical instrument 10 to secure the mesh 402 to the tissue 404. Thus, the magnetic properties of the mesh 402 are manipulated for grasping/positioning/placing the mesh 402 and the tack 502 is ejected/manipulated for securely tacking the mesh 402 on the tissue 404.

Stated differently, the electromagnetic manipulator 14 is in cooperation with at least one tack 502 for performing tacking of the mesh 402. The tack 502 may include a ferromagnetic material incorporated therein. The ferromagnetic properties of the tack 502 allow the tack 502 to be magnetically engaged with the electromagnetic manipulator 14. Additionally, the mesh 402 has a ferromagnetic coating. The ferromagnetic coating responds to electromagnetism emitted by the electromagnetic manipulator 14. The mesh 402 is positioned in proximity to the electromagnetic manipulator 14 to be placed at a surgical site, the mesh 402 being exposed to electromagnetism emitted from the electromagnetic manipulator 14, such that the tacking of the mesh 402 to the tissue 404 of the surgical site is performed.

Referring to FIG. 6A, a perspective view 600A of the surgical instrument 10 of FIG. 1 electromagnetically grasping the mesh 402 and applying a UV light thereafter to the tissue 604 is presented, the mesh 402 having a positive charge coating and the tissue 604 having a negative charge coating, whereas referring to FIG. 6B, a side view 600B of FIG. 6A illustrating the positive charged mesh placed on negative charged tissue of a surgical site is presented.

FIG. 6A depicts the distal end 11 of the surgical instrument 10 of FIG. 1 approaching the mesh 402. The distal end 11 of the surgical instrument 10 includes the electromagnetic manipulator 14 and a UV light source 18. The mesh 402 has magnetic properties.

The magnetic properties of the mesh 402 respond to the electromagnetic manipulator 14 in the activated state, whereas the UV properties of the tissue 604 are activated by the UV light source 18. Thus, the electromagnetic manipulator 14 is used for moving/placing/positioning the mesh 402, whereas the UV light source 18 is used for applying a UV light through the mesh 402 to cure the UV coating of the tissue 604 such that it adheres to the mesh 402.

FIG. 6B depicts the mesh 402 placed on tissue 604. The surgeon manipulates the electromagnetic manipulator 14 in order to achieve proper placement of the mesh 402 on the tissue 604. Once proper placement has been achieved, the surgeon may manipulate the trigger 70 to activate the UV light source 18. The activation of the UV light source 18 enables UV light to be emitted from the distal end 11 to interact with the UV properties of the mesh 402. As such, the mesh 402 may be tacked to the tissue 604 via the UV light interacting with the UV coating of the tissue 604. However, in FIGS. 6A and 6B, the mesh 402 includes a positive charge coating 602 and the tissue includes a negative charge coating 606. Thus, once the mesh 402 is tacked to the tissue 604, the positive charge coating 602 is placed directly over the negative charge coating 606 for providing a secure attachment. In other words, the mesh 402 has a positive charge coating with, for example, methacrylate, whereas tissue 604 of a surgical site has a negative charge coating with, for example, methacrylate for attracting the mesh 402.

Therefore, a method of the exemplary embodiments includes the steps of applying energy to a handle portion of a surgical instrument having a body portion extending distally therefrom, introducing an end effector assembly at a distal end of the body portion and incorporating a UV light source and an electromagnetic manipulator at the end effector assembly. The method also includes the steps of selectively applying electromagnetism via the electromagnetic manipulator to the mesh, selectively applying a UV light emitted from the UV light source to the mesh and UV-tacking the mesh to the surgical site. The mesh includes a ferromagnetic coating that responds to exposure to the electromagnetism emitted from the electromagnetic manipulator.

Referring to FIG. 7A, a perspective view 700A of the surgical instrument 10 of FIG. 1 electromagnetically grasping the mesh 402 and applying a tack 502 thereafter is presented, the mesh 402 having a positive charge coating and the tissue 404 having a negative charge coating, whereas referring to FIG. 7B, a side view 700B of FIG. 7A illustrating the positive charged mesh placed on negative charged tissue of a surgical site including the tack 502 is presented.

FIG. 7A depicts the distal end 11 of the surgical instrument 10 of FIG. 1 approaching the mesh 402. The distal end 11 of the surgical instrument 10 includes the electromagnetic manipulator 14 having the tack 502 (instead of a UV light source as in FIG. 6A). The mesh 402 has magnetic properties.

FIG. 7B depicts the mesh 402 placed on tissue 704. The surgeon manipulates the electromagnetic manipulator 14 in order to achieve proper placement of the mesh 402 on the tissue 704. Once proper placement has been achieved, the surgeon may manipulate the trigger 70 to activate the tack 502. The activation of the tack 502 enables the tack 502 to be ejected from the distal end 11 to secure the mesh 402 to the tissue 704. Therefore, the electromagnetic manipulator 14 is in cooperation with at least one tack 502 for performing tacking of the mesh 402. The tip of the tack 502 includes an electromagnet incorporated therein. However, in FIGS. 7A and 7B, the mesh 402 includes a positive charge coating 702 and the tissue includes a negative charge coating 706. Thus, once the mesh 402 is tacked to the tissue 704, the positive charge coating 702 is placed directly over the negative charge coating 706 for providing a secure attachment. In other words, the mesh 402 has a positive charge coating with, for example, methacrylate, whereas tissue 704 of a surgical site has a negative charge coating with, for example, methacrylate for attracting the mesh 402.

As a result, the magnetic properties of the mesh 402 are manipulated for grasping/positioning/placing the mesh 402 and the tack 502 is ejected/manipulated for securely tacking the mesh 402 on the tissue 704.

Therefore, a method of the exemplary embodiments includes the steps of applying energy to a handle portion of a surgical instrument having a body portion extending distally therefrom, introducing an end effector assembly at a distal end of the body portion and incorporating at least one tack and an electromagnetic manipulator at the end effector assembly. The method also includes the steps of selectively applying electromagnetism via the electromagnetic manipulator to the mesh, selectively applying the at least one tack to the mesh and tacking the mesh to the surgical site. The mesh includes a ferromagnetic coating that responds to the electromagnetism emitted from the electromagnetic manipulator.

In an alternative embodiment, the surgical instrument 10, 60 includes at least one sensor adapted to continuously or intermittently monitor UV light emission from the UV light source 14, 90.

The tissue discussed above for receiving the mesh may possess a photo-curable UV coating thereon. In accordance with the present disclosure, any suitable photo-curable UV coating may be applied to the tissue. As used herein, the term "photo-cured" refers to the reaction of polymerizable groups whereby the reaction can be triggered by actinic radiation, such as UV light. In this application UV-cured can be a synonym for photo-cured. Moreover, photopolymerization refers to an effective method to covalently crosslink polymer chains, producing stable three-dimensional hydrogel networks of varying geometries and physico-chemical properties. In one embodiment, polymers are modified with functional groups (i.e., methacrylates in one embodiment) that undergo free radical polymerization in the presence of a photo-initiator and upon exposure to UV light. Thus, the photo-curable UV coating may include such polymers.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of presently disclosed embodiments. Thus the scope of the embodiments should be determined by the appended claims and their legal equivalents, rather than by the examples given.

Persons skilled in the art will understand that the devices and methods specifically described herein and illustrated in the accompanying drawings are non-limiting exemplary embodiments. The features illustrated or described in connection with one exemplary embodiment may be combined with the features of other embodiments. Such modifications and variations are intended to be included within the scope of the present disclosure. As well, one skilled in the art will appreciate further features and advantages of the present disclosure based on the above-described embodiments. Accordingly, the present disclosure is not to be limited by what has been particularly shown and described, except as indicated by the appended claims.

The invention claimed is:

1. A method of tacking a mesh to a surgical site, the method comprising:
   applying energy to a handle portion of a surgical instrument having a body portion extending distally therefrom;
   introducing an end effector assembly at a distal end of the body portion;
   incorporating at least one tack having a first magnetic polarity and a standalone electromagnetic element at the end effector assembly, the standalone electromagnetic element configured to provide a second magnetic polarity opposite the first magnetic polarity;
   selectively applying electromagnetism to the mesh comprising a positive charge coating;
   placing a negative charge coating on tissue such that the mesh is secured to tissue; and
   activating the standalone electromagnetic element to provide the second magnetic polarity thereby ejecting the at least one tack from the end effector through a pore of the mesh and using the standalone electromagnetic element to tack the mesh at the surgical site;
   wherein the mesh includes a ferromagnetic coating that is responsive to exposure from the electromagnetism emitted from the standalone electromagnetic element.

2. The method according to claim 1, further comprising selectively activating the at least one tack or the standalone electromagnetic element via a trigger mechanism.

3. The method according to claim 1, further comprising placing the positive charge coating of the mesh in registration with the negative charge coating on tissue.

* * * * *